United States Patent [19]

Sugier et al.

[11] 4,122,110

[45] Oct. 24, 1978

[54] PROCESS FOR MANUFACTURING ALCOHOLS, PARTICULARLY LINEAR SATURATED PRIMARY ALCOHOLS, FROM SYNTHESIS GAS

[75] Inventors: André Sugier; Édouard Freund, both of Rueil Malmaison, France

[73] Assignee: Institut Francais du Petrole, France

[21] Appl. No.: 846,486

[22] Filed: Oct. 28, 1977

[30] Foreign Application Priority Data

Oct. 29, 1976 [FR] France .................................. 76 33046

[51] Int. Cl.$^2$ ...................... C07C 29/00; C07C 31/06; C07C 31/08
[52] U.S. Cl. .......................... 260/449.5; 260/449.6 R; 260/449 R; 252/464; 252/465; 252/466 R; 252/470; 252/474
[58] Field of Search .......... 260/449.5, 449 R, 449.6 R

[56] References Cited

U.S. PATENT DOCUMENTS

| | | | |
|---|---|---|---|
| 2,787,628 | 4/1957 | Himmler et al. ................... | 260/449.5 |
| 3,326,956 | 6/1967 | Davies et al. ....................... | 260/449.5 |
| 3,850,850 | 11/1974 | Collins ............................... | 260/449.5 |

FOREIGN PATENT DOCUMENTS 660,678  7/1929  France ..................................... 260/449

*Primary Examiner*—Howard T. Mars
*Attorney, Agent, or Firm*—Millen & White

[57] ABSTRACT

Alcohols, particularly linear saturated primary alcohols, are manufactured from CO and $H_2$ in the presence of a catalyst comprising at least 4 essential elements, copper, cobalt, a third metal selected from chromium, iron, vanadium and manganese, and at least one alkali metal. A preferred method for manufacturing the catalyst is also described; it comprises the use of a complexant, such as citric acid.

12 Claims, No Drawings

PROCESS FOR MANUFACTURING ALCOHOLS, PARTICULARLY LINEAR SATURATED PRIMARY ALCOHOLS, FROM SYNTHESIS GAS

The present invention relates to a catalytic process for manufacturing saturated straight-chain primary alcohols from carbon monoxide and hydrogen.

Two main types of process have been proposed for preparing alcohols from synthesis gases CO + $H_2$: the modified Fischer and Tropsch syntheses with alkali metal containing iron catalysts and the isobutyl synthesis.

As a rule, the processes of the Fischer and Tropsch type have poor selectivity, as well as concerns the nature of the products as the repartition of the molecular weights for a given type of products, and they have poor productivity, usually lower than 5 kg/m$^3$ of catalyst/hour for a given alcohol.

Another known process is the isobutyl synthesis used in Europe between 1935 and 1945; it is analogous to the methanol synthesis and utilizes the same catalyst (zinc chromite) modified by addition of an alkali metal salt, at high pressures and temperatures (respectively 300 to 400 bars, 380° to 450° C.). A representative composition of the main products obtained is the following: methanol (50%), isobutanol (20–40%), n-propanol and higher alcohols; the latter comprise non-linear primary and secondary alcohols (50—50%).

It has been proposed, in the prior art, for these reactions, to use nearly all metals of the periodic classification, either alone or as associations.

The state of the art may be illustrated by the following patents:

French Pat. No. 1,074,045 proposes the use of precipitated catalysts comprising a major proportion of copper and a minor proportion of metal of the iron group with possible addition of known activators, such as alkali metals, zinc or chromium; a copper, iron, potassium catalyst is described.

It is indicated that copper is detrimental to the catalysts containing nickel or cobalt.

The British Pat. No. 317,808 and the French Pat. No. 660,678 disclose catalysts similar to the above ones.

Catalysts containing zinc and chromium with optional additives are disclosed in the Federal German Pat. No. 857,799. Finally the German Pat. No. 544,665 proposes to employ alkali, earth-alkali or earth metals, or rare earth metals, in the absence of heavy metals.

It has been found, and this is the object of the present invention, that certain catalysts could be used in the process of manufacture of linear saturated primary alcohols from mixtures of CO with $H_2$ or CO with $CO_2$ and $H_2$, to obtain the following advantages as compared to the above processes:

the selectivity to alcohols is high; it may be higher than 95%, particularly when using the preferred method for manufacturing the catalyst; practically no hydrocarbons, particularly methane, are formed.

the selectivity to linear saturated primary alcohols in $C_2$ or more is often higher than 70% by weight, which differs from the alcohols obtained by isobutyl synthesis.

the productivity is great, higher than 100 kg of $C_2^+$ alcohols per cubic meter of catalyst per hour, as compared to 20 kg/m$^3$/hour of $C_1$–$C_4$ alcohols for the Fischer - Tropsch method.

the operating conditions differ from those of the prior processes.

In the process as used for the manufacture of alcohols, the pressure is usually between 20 and 250 bars and preferably between 50 and 150 bars, the ratio $H_2$/CO, $CO_2$ is advantageously between 0.4 and 10 and preferably between 0.5 and 4 and the temperature is between 150° and 400° C. and preferably between 220° and 350° C.

The catalysts which are used according to the invention contain at least 4 essential elements, i.e. copper, cobalt, a third metal M selected from chromium, iron, vanadium and manganese and a fourth metal which is an alkali metal A, preferably lithium, sodium or potassium. Zinc is optional. These elements are in the following atomic proportions: $Cu_x Co_y M_z A_v$ (I).

When zinc is present, it is in the atomic proportion $Zn_u$.

In this general formula, $x$ may range from 0.1 to 1, $y$ from 0.1 to 1, $z$ from 0.2 to 1, $u$ from 0 to 0.5 and not above $0.5y$, and $v$ represents 0.001 to 0.25 times the sum $(x + y + z)$. The above formula does not indicate in which form the metals are present. As a general rule, at the end of the manufacture of the catalyst, these metals are present as oxides, although under use conditions, certain oxides may be more or less reduced.

In a preferred catalytic formula, when $x = 1$, $y = 0.2$ to 1.2, $z = 0.1$ to 1 and $v = 0.02$ to 0.2.

The Cu, Co, M and eventually Zn metals are usually present as oxides such as CuO, CoO, $CrO_3$ or heat decomposable salts such as carbonates, sulfates, nitrates, oxalates, tartrates, citrates, acetates or succinates, or in the form of complexes, for example a chromate or vanadate.

When preparing these catalytic compositions, it is preferred to employ manufacture techniques leading to a product of so homogeneous composition as possible, and avoiding segregation of the elements during preparation. Coprecipitation techniques may be used, or techniques making use of thickeners such as gums. Binders may be added, for example alumina, magnesia or cements.

A method of manufacture which leads to catalysts of higher selectivity and which is thus to be preferred, comprises the manufacture of a common solution of the Cu, Co an M metal compounds with the addition of an agent selected from the organic complexant compounds, preferably from:

the organic acids with 2 or more acid groups, for example oxalic, malonic, succinic or glutaric acid, acid-alcohols, for example glycolic, lactic, malic, tartric or citric acid, aminoacids, for example aminoacetic acid, alanine or leucine.

Water is evaporated from the resulting solution, for example by heating at 200°–600° C., which yields a powder which is agglomerated, preferably with an aluminous cement containing alumina and lime in the form of calcium aluminate.

Metal A may be supplied with the other metals, in the form of a soluble salt, or thereafter to the powder or to the formed catalyst.

Shaping may be effected according to conventional techniques of the art, particularly by tabletting or extrusion, or by pill-forming while adding, for example, aluminous refractory cements which, further to their binding properties, have a co-catalytic effect due to their basicity. The preferred aluminous cements contain 40–85% b.w. of $Al_2O_3$ and 15–30% of CaO with optionally small amounts of other components. Alumina and lime are present in major portion in the form of calcium aluminates.

Drying and calcination, for example at about 400° to 1000° C., are the usual final steps.

The incorporation of the alkali metal(s) may occur before shaping of the catalyst or thereafter, for example by impregnation with a solution of soluble salts or hydroxides of one or more elements of the group Ia of the periodic classification. This addition may also take place before the drying and calcining steps by addition of a solution of one or more soluble compounds of metals of group Ia; it may also take place with chromates or dichromates of one or more elements of group Ia.

CATALYST A (COMPARISON CATALYST)

400 ml of water and then 80 g of citric acid are added to a mixture of 160 g of chromic anhydride $CrO_3$ with 115 g of copper carbonate 2 $CuCO_3$, $Cu(OH)_2$. The resulting solution is dried for 2 hours at 200° C. and then heated in air at 450° C. The resulting powder of composition $(Cr_2O_3)_{0.4}$ $(CuO)_1$ is made to tablets of 5 × 5 mm with are then impregnated with a potassium hydroxide solution, so as to introduce 2% b.w. of potassium, calculated as $K_2O$. The tablets are heated for 2 hours at 400° C.

The resulting catalyst is in the form of oxides with the metals present in the following relative proportions:

$$Cr_{0.8} \, Cu_1 \, K_{0.06}$$

CATALYSTS $B_1$ AND $B_2$ 450 ml of water are added to a mixture of 160 g of chromic anhydride $CrO_3$ with 483 g of copper nitrate $Cu(NO_3)_2$, 3 $H_2O$ and 233 g of cobalt carbonate 2 $CoCO_3$, 3 $Co(OH)_2$, $n$ $H_2O$ containing 50.5% b.w. of cobalt; when the gas evolution has ceased, 100 g of citric acid are added. The resulting solution is dried at 200° C. for 2 hours and then heated in air for 3 hours at 450° C.

Half of the resulting powder of molar composition $(Cr_2O_3)_{0.4}$, $(CuO)_1$, $(CoO)_1$ is made to tablets of 5 × 5 mm. These tablets are then impregnated with a potassium hydroxide solution to introduce an amount of potassium, expressed as $K_2O$, of 2% b.w. After 2 h heating at 400° C., catalyst $B_1$ is obtained, wherein the metals are present in the following molar proportions: $Cu_1 \, Co_1 \, Cr_{0.8} \, K_{0.09}$. The other half of the powder is admixed in totality with a refractory aluminous cement of the "Super Secar" type of composition in % b.w.: $Al_2O_3$: 81, CaO: 17, $Na_2O$: 0.8, $Fe_2O_3$: 0.1, plus others. This mixture is obtained from 70% of powder obtained according to the above method and 30% of aluminous cement.

The resulting mixture is then made to 5 mm pills in a pill-maker by pulverization of a 5% b.w. aqueous solution of potassium hydroxide, so that the potassium content, expressed as $K_2O$, of the resulting product is 1.7% b.w.

The pills are then heated in air for 2 hours at 400° C.; the resulting catalyst $B_2$ contains metals in the following molar proportions: $Cu_1 \, Co_1 \, Cr_{0.8} \, K_{0.09}$ + aluminous cement.

CATALYST $B'_1$ 160 g of chromic anhydride $CrO_3$, 483 g of copper nitrate $Cu(NO_3)_2$, 3 $H_2O$ and 582 g of cobalt nitrate $Co(NO_3)_2$, 6 $H_2O$ are dissolved into 450 ml of water. The solution is dried for 2 hours at 200° C. and then heated in air for 3 hours at 450° C. The resulting powder is made to tablets of 5 × 5 mm size, which are impregnated with a potassium hydroxide solution, so as to introduce a potassium content, expressed as $K_2O$, of 2% b.w. After 2 hours heating at 400° C., there is obtained catalyst $B'_1$ where the metals are present in the following molar proportions: $Cu_1 \, Co_1 \, Cr_{0.8} \, K_{0.09}$.

CATALYST $B_3$

2 Liters of an aqueous solution of 483 g of copper nitrate $Cu(NO_3)_2$, 3 $H_2O$ and 582 g of cobalt nitrate $Co(NO_3)_2$, 6 $H_2O$ are quickly added to 3 liters of an aqueous solution, heated to 60° C., of 5 moles of sodium carbonate. The resulting precipitate is decanted, carefully washed, dried at 200° C. and then impregnated with an aqueous solution of 18.6 g potassium chromate, so as to introduce 2% of potassium, expressed as $K_2O$, and then with a solution of 200 g of ammonium dichromate.

The product is dried for 2 hours at 200° C. and then heated in air at 450° C. for 2 hours. The resulting powder is made to tablets of 5 × 5 mm size.

Catalyst $B_3$ is thus obtained, where the metals are present in the following molar proportions:

$$Cu_1 \, Co_1 \, Cr_{0.8} \, K_{0.09}$$

CATALYST C 450 ml of water and 100 g of citric acid are added to a mixture of 160 g chromic anhydride $CrO_3$, 483 g copper nitrate $Cu(NO_3)_2$, 3 $H_2O$, 163 g cobalt carbonate of 50.5% b.w. cobalt content and 37.6 g zinc carbonate $ZnCO_3$. The resulting solution is dried for 2 hours at 200° C. and then treated for 2 hours at 450° C.

The resulting powder is made to 5 × 5 mm tablets and then impregnated with a potassium hydroxide solution to introduce 2% b.w. of potassium, expressed as $K_2O$.

The tablets are then treated for 2 hours at 400° C. The resulting catalyst C contains the metals in the following molar proportions:

$$Cu \, Co_{0.7} \, Zn_{0.3} \, Cr_{0.8} \, K_{0.09}$$

CATALYSTS D, E, F

6 Liters of an aqueous solution of 6 moles copper nitrate and 6 moles cobalt nitrate are added to 9 liters of an aqueous solution at 60° C. of 16 moles of sodium carbonate. The resulting precipitate is decanted, washed and dried at 200° C. The resulting powder is made to three equal parts.

Catalyst D: One third of the powder is impregnated with a solution containing 1.6 mole of manganese nitrate and then dried at 200° C. and treated 2 hours at 450° C. The resulting powder is made to 5 × 5 mm tablets which are impregnated with a solution of potassium hydroxide, so as to introduce 2% b.w. of $K_2O$. After a 2 hours treatment at 400° C., there is obtained catalyst D where the metals are present in the following molar proportions:

$$Cu \, Co \, Mn_{0.8} \, K_{0.12}$$

Catalyst E: One third of the powder is impregnated with a solution containing 1.6 mole of iron nitrate and then dried at 200° C. and heated in air for 2 hours at 450° C. The resulting powder is made to tablets and impregnated with potassium hydroxide and heat treated as catalyst D; the resulting catalyst E has the molar composition:

$$Cu\ Co\ Fe_{0.8}\ K_{0.12}$$

Catalyst F: The last third of the powder is impregnated with a solution containing 1.6 mole of ammonium vanadate and then dried at 200° C. The resulting powder is shaped, impregnated with potassium hydroxide and heat treated as the catalysts D and E. Catalyst F is thus obtained; its molar composition is $Cu\ Co\ V_{0.8}\ K_{0.12}$.

CATALYST D'

600 ml of water is added to a mixture of 483 g of copper nitrate Cu (NO$_3$)$_2$, 3 H$_2$0, 233 g of cobalt carbonate 2 Co CO$_3$, 3 Co (OH)$_2$, 4 H$_2$O of 50.5% b.w. cobalt content and 402 g of manganese nitrate Mn (NO$_3$)$_2$, 4 H$_2$O; after gas evolution, 140 g of citric acid is added. The resulting solution is dried for 2 hours at 200° C. and then heated in air for 3 hours at 450° C. The resulting powder is made to tablets of 5 × 5 mm size which are thereafter impregnated with a potassium hydroxide solution, so as to introduce 2% b.w. of potassium, expressed as K$_2$O. After 2 hours heating at 400° C., there is obtained catalyst D' of same composition as catalyst D.

CATALYST E'

The procedure is as for catalyst D', except that manganese nitrate is replaced by 646 g of iron nitrate Fe (NO$_3$)$_3$, 9 H$_2$O. The resulting catalyst E' has the same composition as catalyst E.

The activity of the so-prepared catalysts for the synthesis of linear primary alcohols from mixtures of CO, CO$_2$ and H$_2$ is determined as the amount, expressed as grams per hour and per gram of catalyst, of the products obtained by passing a gas mixture of the composition:

| CO | = | 19 | H$_2$ | = | 66 |
|---|---|---|---|---|---|
| CO$_2$ | = | 13 | N$_2$ | = | 2 | on the catalysts at diverse pressures, temperatures and space velocities.

The results are given in the following Table, where the following abbreviations have been used:
  VVH = volume (NTP) of the reactants per hour and per volume of catalyst.
  T = temperature in degrees Celsius
  P = pressure in bars
  D.M.E. = dimethylether.

The selectivity to alcohols is expressed as the ratio $$\frac{\text{moles of CO + CO}_2 \text{ converted to alcohols}}{\text{moles of CO + CO}_2 \text{ converted}}$$

It is determined at a VVH of 4,000, a temperature of 250° C. and a pressure of 60 bars by passage over the catalysts of a gas mixture of composition:

| CO | = | 19 | H$_2$ | = | 66 |
|---|---|---|---|---|---|
| CO$_2$ | = | 13 | N$_2$ | = | 2 |

The following results have been obtained:

| CATALYST | SELECTIVITY |
|---|---|
| B$_1$ | 97 |
| B$_3$ | 94 |
| B'$_1$ | 89 |
| D | 84 |
| D' | 95 |
| E | 82 |
| E' | 96 |

These results show that the highest selectivity is obtained when using the method of evaporation in the presence of citric acid (catalyst B$_1$), as compared to the coprecipitation (catalyst B$_3$) and the evaporation without citric acid (B'$_1$). The selectivity of the catalysts D' and E' (citric acid method) is also higher than that of the catalysts D and E (coprecipitation) respectively.

What we claim is:

1. A process for manufacturing linear saturated primary alcohols, by reacting carbon monoxide with hydrogen at a pressure between 20 and 250 bars and a temperature between 150° and 400° C., in the presence of a catalyst, characterized in that the catalyst contains at least 4 essential elements:
    (a) copper
    (b) cobalt
    (c) at least one element M selected from chromium, iron, vanadium and manganese, and
    (d) at least one alkali metal A, in the following atomic proportions: $Cu_x Co_y M_z A_v$ where $x$ is from 0.1 to 1, $y$ from 0.1 to 1, $z$ from 0.2 to 1 and $v$ from 0.001 to 0.25 times the sum ($x + y + z$).

2. A process according to claim 1, wherein $y = 0.2$ to 1.2, $z = 0.1$ to 1 and $v = 0.02$ to 0.2 for $x = 1$.

3. A process according to claim 1, wherein zinc is also present in atomic proportion $Zn_u$ where $u$ has a value of 0 to 0.5, although not above 0.5 $y$.

4. A process according to claim 1, wherein a binder selected from alumina, magnesia or cements is also present.

| | | | | YIELD IN g/h/g CATALYST | | | | | | |
|---|---|---|---|---|---|---|---|---|---|---|
| CATA | P | T | VVH | methanol | D.M.E. | ethanol | n. pro-panol | i. pro-panol | n. buta-nol | i. buta-nol |
| A | 60 | 250 | 4000 | 0.104 | 0.002 | 0.008 | <0.001 | <0.001 | <0.001 | <0.001 |
| B$_1$ | 60 | 250 | 4000 | 0.076 | <0.001 | 0.125 | 0.063 | 0.006 | 0.045 | <0.001 |
| | | 270 | | 0.99 | <0.001 | 0.163 | 0.080 | 0.008 | 0.050 | <0.001 |
| | 120 | 250 | 4000 | 0.130 | <0.001 | 0.244 | 0.135 | 0.021 | 0.108 | 0.002 |
| | | | 8000 | 0.208 | <0.001 | 0.341 | 0.192 | 0.027 | 0.150 | 0.003 |
| B$_2$ | 60 | 250 | 4000 | 0.063 | <0.001 | 0.117 | 0.058 | 0.008 | 0.040 | <0.001 |
| B$_3$ | 60 | 250 | 4000 | 0.080 | <0.001 | 0.128 | 0.069 | 0.005 | 0.047 | <0.001 |
| C | 60 | 250 | 4000 | 0.081 | 0.002 | 0.119 | 0.064 | 0.008 | 0.040 | <0.001 |
| D | 60 | 250 | 4000 | 0.065 | <0.001 | 0.108 | 0.054 | 0.010 | 0.039 | <0.001 |
| E | 60 | 250 | 4000 | 0.056 | <0.001 | 0.111 | 0.052 | 0.015 | 0.037 | <0.001 |
| F | 60 | 250 | 4000 | 0.063 | 0.008 | 0.104 | 0.030 | 0.08 | 0.029 | <0.001 |

5. A process according to claim 1, wherein the catalyst contains copper, cobalt, chromium and at least one alkali metal.

6. A process according to claim 1, wherein the catalyst contains copper, cobalt, iron and at least one alkali metal.

7. A process according to claim 1, wherein the catalyst contains copper, cobalt, vanadium and at least one alkali metal.

8. A process according to claim 1, wherein the catalyst contains copper, cobalt, manganese and at least one alkali metal.

9. A process according to claim 1, wherein the catalyst has been obtained by a method comprising dissolving at least one compound of each of the metals Cu, Co and M into water containing a complexant organic compound selected from the group consisting of organic polyacids, the acid-alcohols and the amino acids, followed with evaporating water.

10. A process according to claim 9, wherein the complexant compound is citric acid.

11. A process according to claim 9, wherein, after evaporation of water, a powder is obtained, which is admixed with an aluminous cement, shaped and calcined at 400°–1000° C.

12. A process according to claim 1, wherein carbon dioxide is also present.

* * * * *